United States Patent
Kecman et al.

(10) Patent No.: US 8,617,169 B2
(45) Date of Patent: Dec. 31, 2013

(54) ADJUSTABLE SURGICAL INSTRUMENT

(75) Inventors: Maja Kecman, London (GB); Lisa Stroux, Heidelberg (DE)

(73) Assignee: Depuy International Limited (GB)

( * ) Notice: Subject to any disclaimer, the term of this patent is extended or adjusted under 35 U.S.C. 154(b) by 299 days.

(21) Appl. No.: 12/679,024

(22) PCT Filed: Sep. 19, 2008

(86) PCT No.: PCT/GB2008/003191
§ 371 (c)(1),
(2), (4) Date: Jul. 22, 2010

(87) PCT Pub. No.: WO2009/037479
PCT Pub. Date: Mar. 26, 2009

(65) Prior Publication Data
US 2011/0040302 A1   Feb. 17, 2011

(30) Foreign Application Priority Data

Sep. 21, 2007   (GB) .................................. 0718418.7

(51) Int. Cl.
*A61B 17/58*   (2006.01)
(52) U.S. Cl.
USPC .......................................................... 606/88
(58) Field of Classification Search
USPC ................. 606/82, 86 R–90, 96–98
See application file for complete search history.

(56) References Cited

U.S. PATENT DOCUMENTS

| 5,228,459 | A | * | 7/1993 | Caspari et al. ................. 128/898 |
| 5,306,276 | A | * | 4/1994 | Johnson et al. ............. 606/86 R |
| 5,667,511 | A | * | 9/1997 | Vendrely et al. ................. 606/88 |
| 6,090,114 | A | | 7/2000 | Matsuno |
| 6,267,762 | B1 | | 7/2001 | Millard |
| 2004/0015173 | A1 | * | 1/2004 | Irving ............................. 606/88 |
| 2005/0182415 | A1 | * | 8/2005 | Steffensmeier et al. ........ 606/88 |
| 2006/0235420 | A1 | | 10/2006 | Irving |
| 2006/0241639 | A1 | | 10/2006 | Kuczynski |

FOREIGN PATENT DOCUMENTS

EP   551572 A2   7/1993
GB   2398011 A   8/2004

OTHER PUBLICATIONS

PCT International Search Report and Written Opinion PCT/GB2008/003191 dated Nov. 19, 2008.
UK Search Report 0718418.7 dated Dec. 10, 2007.

* cited by examiner

*Primary Examiner* — Todd Manahan
*Assistant Examiner* — Eric S Gibson

(57) ABSTRACT

A surgical instrument is described which comprises an alignment guide having a first part including a distal end and a second part having a proximal end. The first part is attached to the second part by a pivot mechanism so that the first part can be tilted relative to the second part. A brace is attached toward the proximal end of the alignment guide for attaching the instrument to a limb of a patient. A component is attached toward the distal end of the alignment guide. The pivot mechanism is configured so that tilting the first part does not substantially change the separation between the component and the brace.

13 Claims, 5 Drawing Sheets

ADJUSTABLE SURGICAL INSTRUMENT

CROSS REFERENCE TO RELATED APPLICATION

This application is a National Stage 35 U.S.C. 371 of International Patent Application PCT/GB2008/003191 filed Sep. 19, 2008.

The present invention relates to a surgical instrument, and in particular to an alignment guide having angular adjustment.

BACKGROUND OF THE INVENTION

Various instruments and devices are used during orthopaedic arthroplasty procedures, such as, e.g., a knee arthroplasty procedure, to assist and guide the positioning of various instruments and devices used during the procedure. For example, FIG. 1 shows a side view of a prior art external tibial alignment guide 10 attached to the lower leg of a patient which can be used during a knee arthroplasty procedure. The alignment guide 10 is used to position a tibial cutting block 12 against the tibial tubercle to perform a proximal tibial cut. The alignment guide includes an ankle clamp 14 by which the guide 10 is fixed distally to the patient's lower leg 16. The ankle clamp includes a block and a pair of clamps which engage around the ankle. The cutting block is attached to a telescopically extendable support member 18. The support 18 provides an external alignment guide by which the attached cutting block can be positioned and aligned relative to the longitudinal, inferior-superior axis of the tibia. That is, the support member can be aligned with the axis of the tibia.

The tibial resection position can be set using a stylus in combination with the cutting block 12 and once the height is selected, the cutting block can be pinned in place and the tibial cut performed.

However, only the height of the cutting block can be adjusted. Therefore it is not possible to otherwise alter the position of the cutting block so as to make a cut at a desired or planned position.

Therefore, there is a need for a more flexible alignment guide with greater adjustability.

BRIEF SUMMARY OF THE INVENTION

According to a first aspect of the present invention, there is provided a surgical instrument, comprising: an alignment guide having a first part including a distal end and a second part having a proximal end, and wherein the first part is attached to the second part by a pivot mechanism so that the first part can be tilted relative to the second part; a brace attached toward the proximal end of the alignment guide for attaching the instrument to a limb of a patient; a component attached toward the distal end of the alignment guide.

Hence, the instrument of the invention provides greater adjustability as the alignment guide can be tilted to position the component at a preferred position relative to a part of the limb of a patient.

Preferably, the pivot mechanism is configured so that tilting the first part does not substantially change the separation between the component and the brace. Hence, it is not necessary to adjust the length of the instrument after the alignment guide has been tilted.

The pivot mechanism can include a curved member. The separation between the position of the curved member and the position of a part of the component can have a length substantially the same as the radius of curvature of the curved member. Hence, in this way, the centre of pivoting is provided in a preferred part of the component so that the height of the component does not substantially alter as the part is tilted.

The pivot mechanism can include a sleeve attached to the first portion. The sleeve can be slidably mounted on the curved member.

The pivot mechanism can be slid along a longitudinal axis of the second part to alter the overall length of the instrument.

The pivot mechanism can include a clamp to hold the pivot mechanism at a particular tilt angle.

The pivot mechanism can include a scale which can display a current degree of tilt of the first part of the instrument.

The brace can project outwardly toward a rearward side of the instrument. The pivot mechanism can project outwardly toward a forward side of the instrument in a generally opposite direction to the brace. By placing the pivot mechanism on a generally opposite side of the instrument to the brace, more space is available for accepting the pivot mechanism. It is also easier to operate the pivot mechanism as the patient's limb will not interfere.

The first part can include a hollow region extending along a portion of the length of the first part. The hollow region can receive at least a portion of the second part. A rearward side of the first part can include an elongate aperture, or no rear face, so that the portion of the second part can be released from the first part when the first part is tilted relative to the second part. Hence, the extra length of the second part which allows the overall length of the instrument to be extended does not interfere with allowing the first part to be pivoted.

The instrument can further include a base. The proximal end of the alignment guide can be slidably mounted on the base to allow the lateral position of the alignment guide to be adjusted relative to the brace. Hence, the position of the alignment guide in a medial-lateral direction of the patient can be adjusted or fine tuned.

A further aspect of the invention can include a method of use or operation of the instrument aspect of the invention as indicated above and described in detail below.

BRIEF DESCRIPTION OF THE DRAWINGS

An embodiment of the invention will now be described, by way of example only, and with reference to the accompanying drawings, in which.

DETAILED DESCRIPTION OF THE INVENTION

Figure 1:
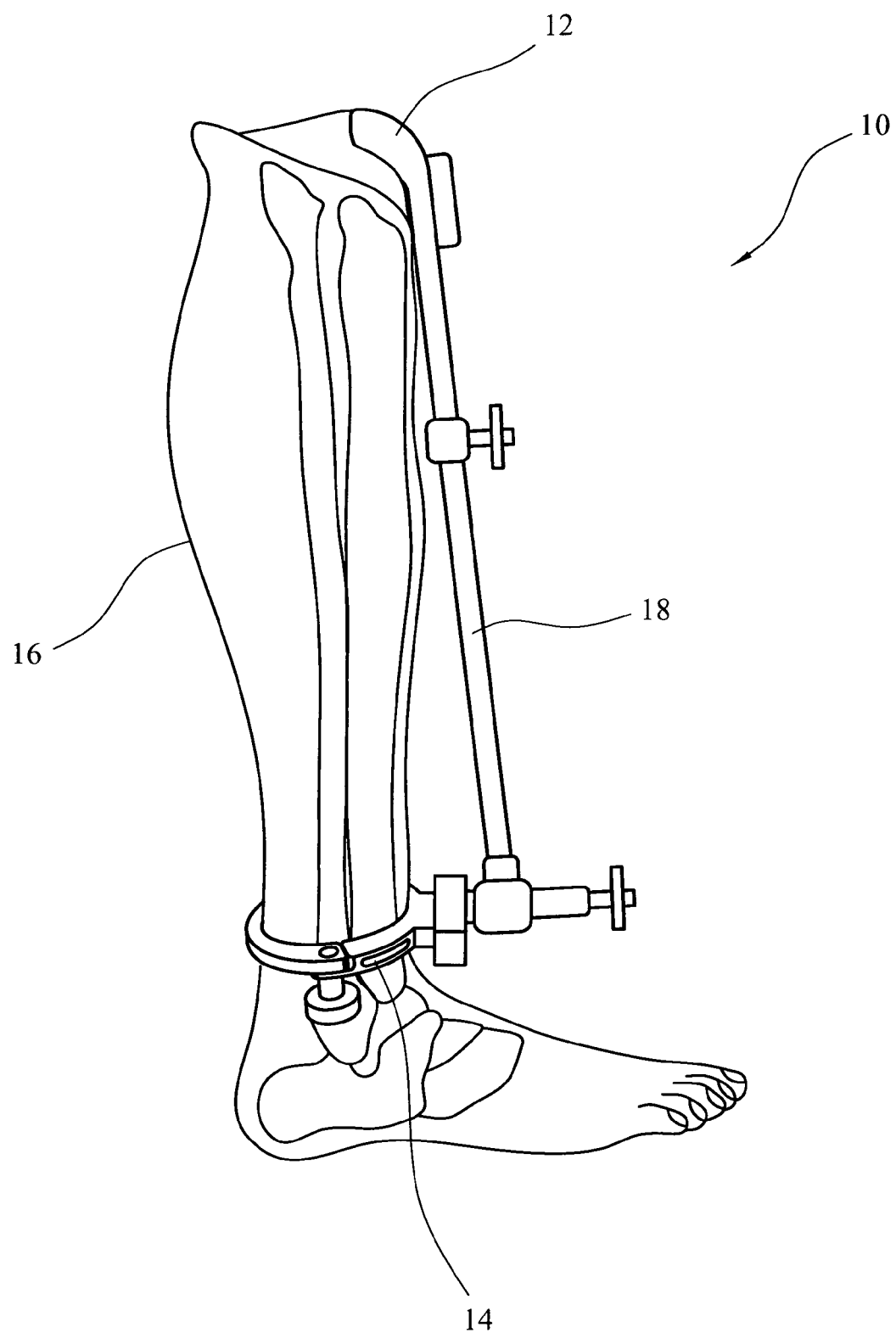
FIG. 1 shows a side view of a prior art external tibial alignment guide.

Similar items in different Figures share common reference numerals unless indicated otherwise.

Figure 2:
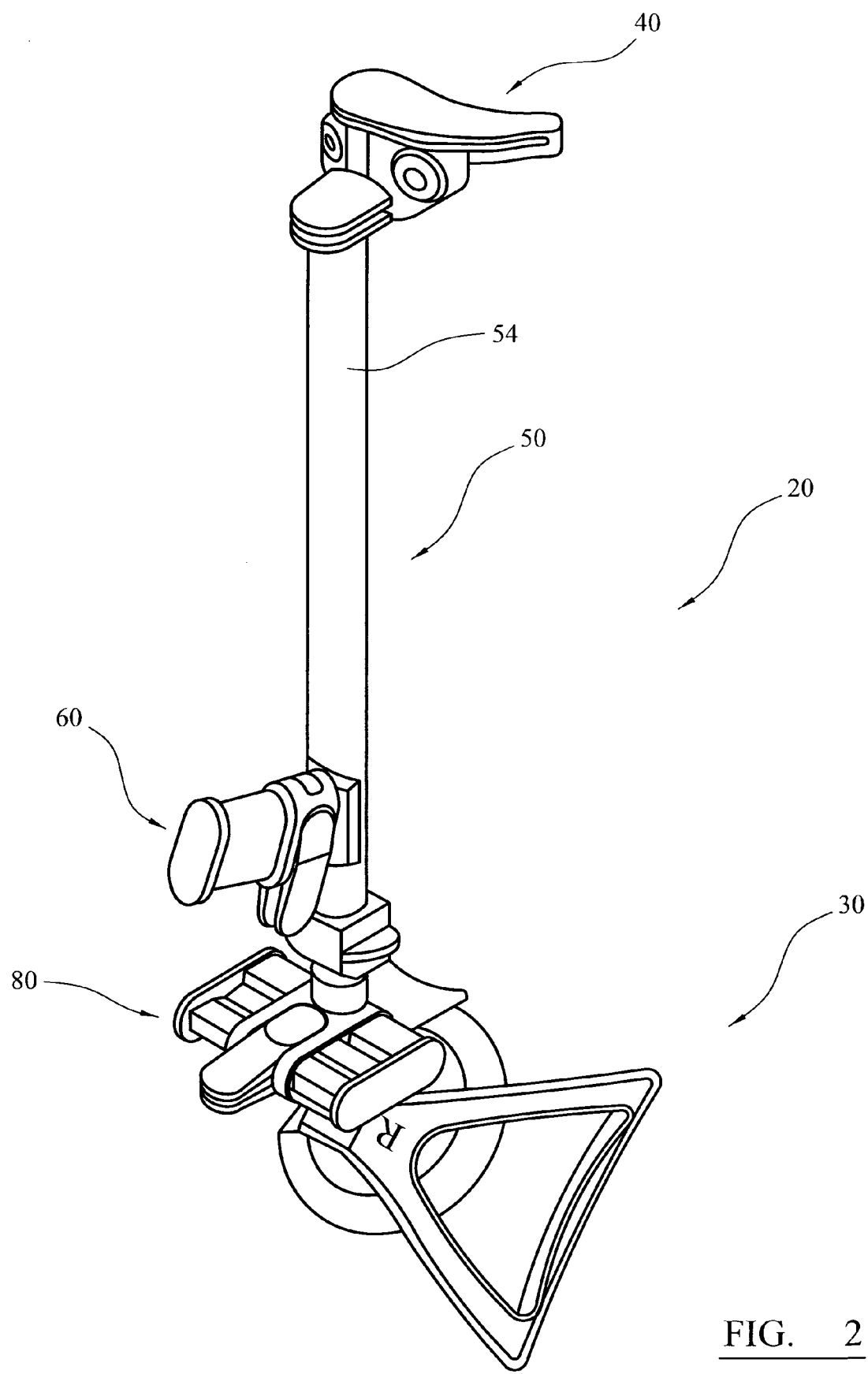
FIG. 2 shows a perspective view of an alignment guide including the invention.
Figure 3:
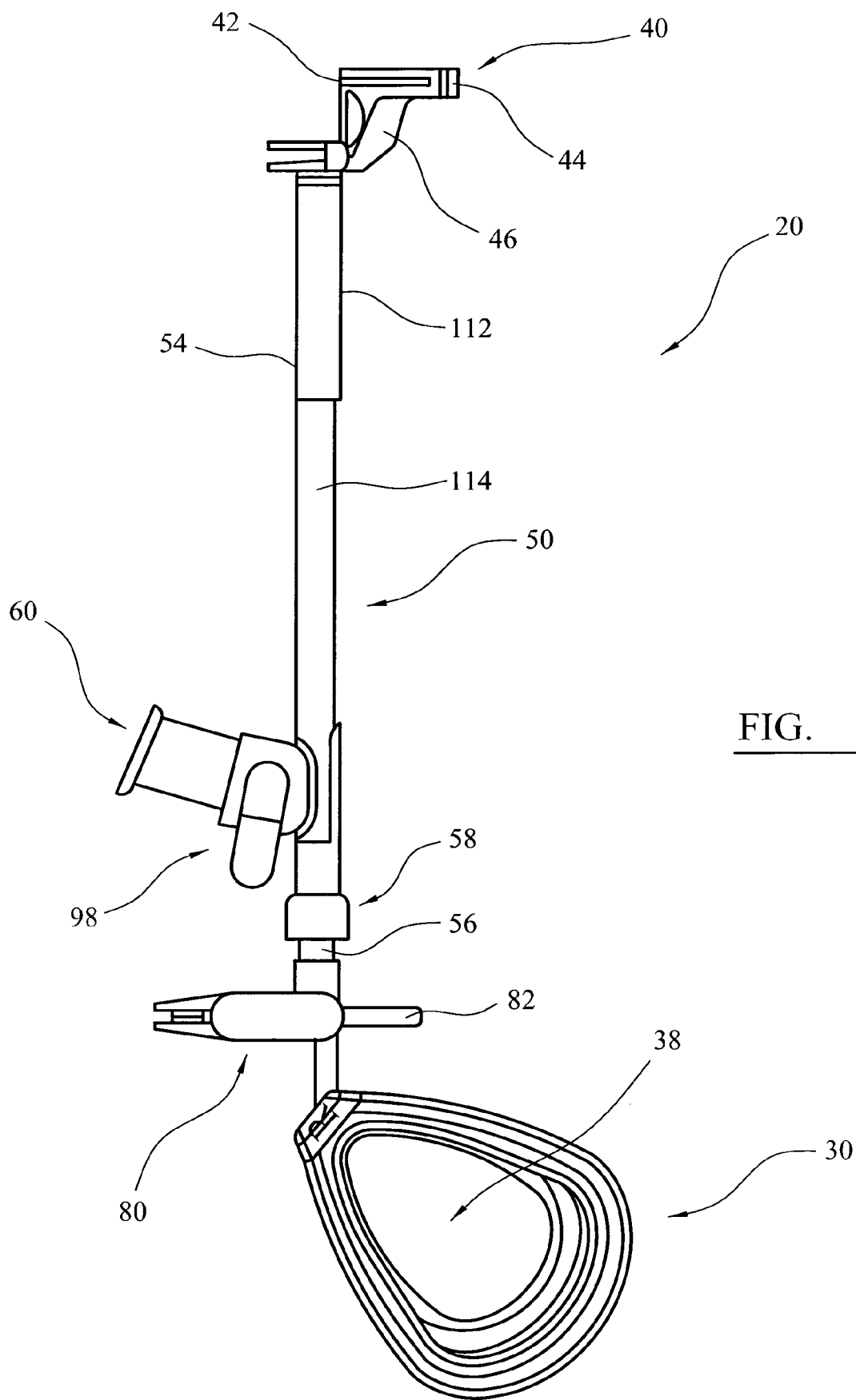
FIG. 3 shows a side elevation of the alignment guide shown in FIG. 2 with a second part at a first position.
Figure 4:
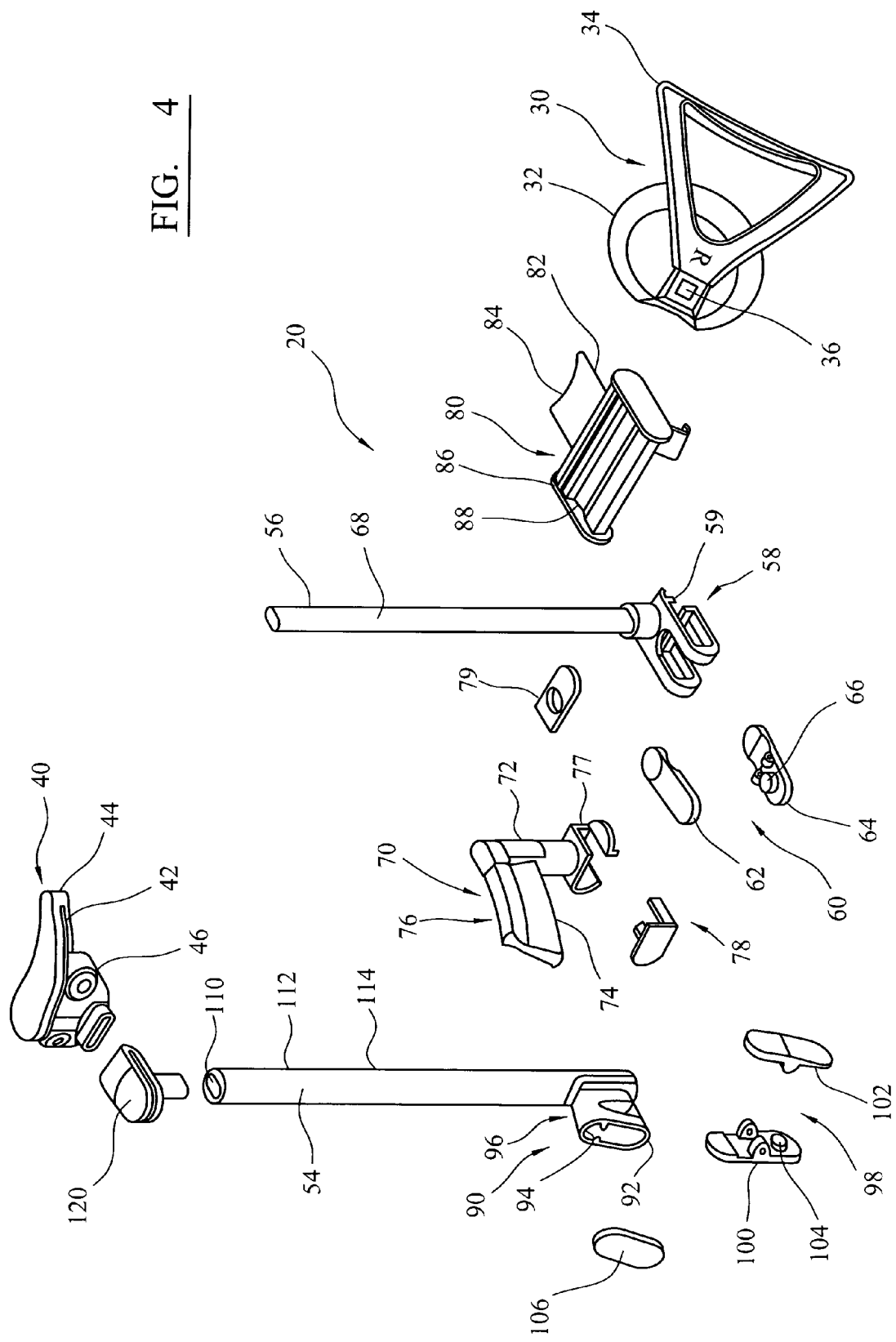
FIG. 4 shows an exploded perspective view of the alignment guide shown in FIG. 2.

FIG. 2 shows a perspective view of an instrument 20 according to an embodiment of the present invention. FIG. 3 shows a side view of instrument 20 and FIG. 4 shows a perspective view of the exploded instrument, illustrating its constituent parts.

The instrument 20 generally includes a brace 30 toward a proximal end of the instrument for attaching the instrument to a patient as will be described in greater detail below. A component 40 is attached to a distal end of the instrument 20 and in the embodiment illustrated the component is in the form of a cutting guide. Instrument 20 also includes a further component 50 through which the cutting guide and brace are attached at respective ends. In the embodiment illustrated, the further component 50 is an external alignment guide. The alignment guide 50 includes a pivot mechanism 60 which allows a first, top portion of the alignment guide to pivot relative to a second, lower part of the alignment guide as will be described in greater detail below.

Brace 30 is attached to a base member 80 by a snap-fit mechanism which allows the brace to be releasably attached to the instrument. Base 80 has a generally planar member 82 extending from a rearward portion and presenting a curved edge 84. The shape and dimensions of member 82 are chosen to allow curved edge 84 to abut against a portion of the surface of the shin of a patient during use of the instrument. Base 80 includes a groove 86 and a curved trough 88 extending there across in a generally lateral or transverse direction.

The lower part or portion of the alignment guide component 56 includes a foot portion 58 having a generally U-shaped construction and adapted to engage with base 80 with rib 59 engaging trough 86 to allow sliding translation relative to base 80. A clamp assembly 60 includes first and second ... members 62, 64 and spring 60 which are attached to foot 58 by a metal pin and which can engage with trough 88 in use to prevent sliding.

Lower part 56 of the alignment guide includes a solid elongate member 68 extending from the foot 58 having a generally rectangular shape with a pair of opposed flat sides and a pair of opposed curved sides.

A first part 70 of the pivot mechanism 60 includes a generally hollow support 72 with a curved member 74 extending away therefrom. Curved member 74 bears a plurality of angular indicia 76 by an uppermost surface thereof. The first part 70 of the pivot mechanism includes a clip assembly 78 toward a lower end thereof. The clip assembly includes a generally hollow housing 77 having an aperture in a lower surface thereof and a clip plate 79 including a similar aperture. A spring component is also provided within the clip mechanism.

The member 68 of the lower portion 56 of the alignment guide passes through the apertures and hollow portions of the first part of the pivot assembly. With the clip plate 79 depressed against the action of the spring, the pivot assembly can be translated along the longitudinal axis of the member 68 to provide adjustment of the overall height of the instrument. The spring member acts against clip plate 79 to trap member 68 against the edges of the aperture in the clip plate to prevent translation and hence lock the height of the instrument.

The pivot assembly 60 includes a second part 90 provided toward an end of the second part 54 of the alignment guide. The second part of the pivot assembly 90 is in the form of a rounded, curved sleeve 92 having projections 94 on an inner portion thereof to mate with corresponding recesses in the curved member 74. An aperture 96 is provided in an upper surface enabling a one of the angular indicia 76 to be displayed, depending on the current position of the sleeve 92 along curved member 73. A clamp assembly 98 is also provided including first and second clamp drawers 100, 102 and a spring 104. Clamp assembly 98 is attached to sleeve 92 by a pin passing through the clamp drawers 100, 102 and into receiving apertures of the sleeve 92. An end stop plate 106 is also provided attached to a free end of the curve member 74 and sized to prevent free end of curve member 74 escaping from sleeve 92.

The second upper part 54 of the alignment guide has a generally circular cylindrical construction including a central aperture 110 running along its entire length. The aperture is shaped and dimensioned to receive member 68 so that upper part 54 can slide along the longitudinal axis of member 68. An upper region 112 has a closed cylindrical form while a lower region 114 has an open rear portion, as illustrated best in FIG. 3, having a generally C or U-shaped cross-section. The open portion is shaped in dimensions to allow member 68 to escape from within upper part 54 when upper part 54 is tilted relative to lower part 56.

Cutting block 40 is attached to the distal end of the alignment guide 50 by a spring clip 120 attached by a mail connector to which engages in the aperture 110 of upper part 54. Spring clip 120 allows various different components to be selectively attach to the instrument. In the illustrated embodiment the component is a cutting block 40 suitable for making a tibial cut during a knee arthroplasty procedure. Cutting block 40 includes a slot 42 passing through a generally plate-like curved upper portion 44 attached to a main body 46. Body 46 includes a plurality of coals for accepting a drill-bit to allow holes to be drilled in the patient's bone in use to accept pins for attaching the cutting guide 40 to the patient.

Figure 5:
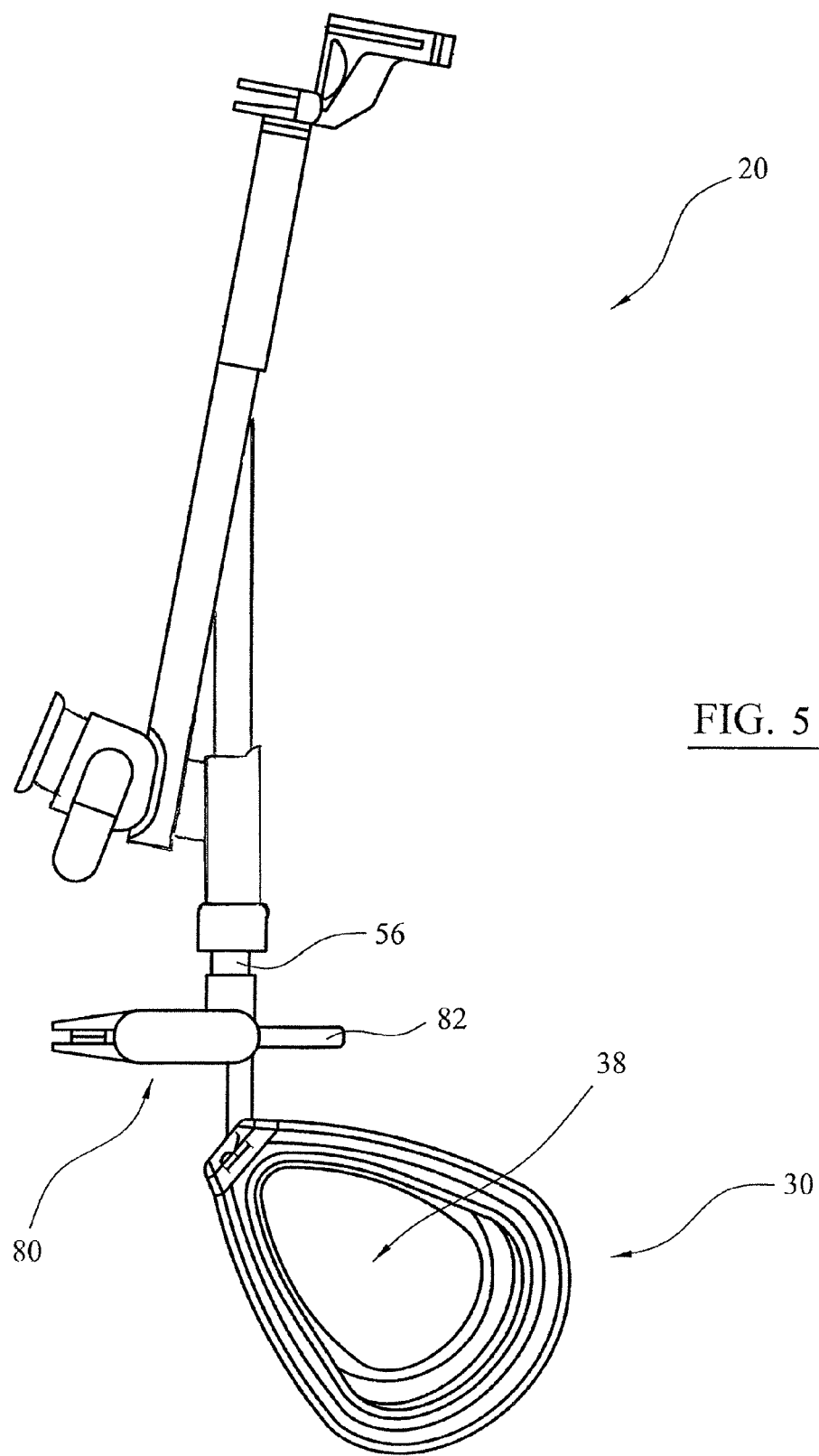
FIG. 5 shows a side elevation of the alignment guide shown in FIG. 2 with a second part at a first position.

The curved member 64 of the pivot mechanism 60 has a radius of curvature centered on a point in the cutting block. Owing to this geometry, as is depicted in FIG. 5, when the sleeve 92 is slid along curved member 74, the upper part 54 of the alignment guide tilts relative to the lower part 56, but the overall length of the instrument does not change. That is the height of at least a portion of the cutting block 40 above the brace does not significantly increase or decrease 25 as the upper part of the alignment guide is effectively pivoting about a point located in the component. Therefore, the angle of the component 40 relative to the remainder of the instrument can be altered, without changing the overall length or height of the instrument. Therefore, in use, a surgeon can alter the angle of the cutting block 40 without having to then re-adjust the overall height of the instrument. The pivot mechanism is provided and 30 configured so as to be able to use an arc (and therefore a proper angle) to set the posterior slope rather than a line (as occurs for prior art device) and to have a proximal pivoting reference to set the posterior slope which is independent of tibial length.

Instrument 20 includes brace 30 by which the instrument can be attached to and support on a patient. Although the embodiment illustrating the invention includes an alignment guide, it will be appreciated that in other embodiments, the brace 30 may be supporting other types of instruments or components relative to a patient's body. In this exemplary embodiment, instrument 20 is an external alignment guide including a tibial cutting block 40. The alignment guide 50 allows the cutting block to be aligned relative to the longitudinal axis of the tibia and also allows the height and angular position of the cutting block 40 to be adjusted to allow a tibial cut to be performed at a planned or preferred position and/or orientation.

The brace 30 includes a first 32 and a second 34 member on generally opposite sides of the brace 30. The members 32, 34 are attached to a common central or bridge portion 36 including an aperture part of a snap-fit fastener by which the brace 30 can be releasably attached to a co-operating part of base 80. Each member 32, 34 is in the form of a loop with a open hole or aperture defined thereby. The loop is formed from a ribbon or band material. The band material has a complex shape and curves in a number of directions. Firstly, the band of material is curved because its transverse dimension provide some spring force. Further, the band of material is curved to define a generally concave formation. Each loop is formed to define a generally pear or tear-dropped aperture 38 which is sized and shaped to accept a respective malleolus of the patient.

The entire brace component 30 is made from a resilient plastics material so that the brace is generally springy so that it can be push-fit onto the ankle of a patient so that the members 32, 34 encircle the malleoli and the resilient material of the brace causes the brace to securely grip the ankle of the patient and hold the instrument in place.

The brace can be made from a suitable plastics material such as various types of polymers, including polyurethane, ABS, Nylon or polypropylene. The plastics materials are selected to have a suitable elasticity and flexibility to be attached to and grip a range of different sizes of ankle in use. In other embodiments, the brace could be made from any suitable springy material, such as metals, alloys, composite materials, high yield stress metals, and hybrid metal and plastics.

As described above, the shapes of the members are adapted or configured so as to ensure that they wrap around the malleoli in use. The apertures in the brace allow the surgeon to feel the malleoli so that he is reassured of the correct positioning of the instrument. Dimensions of the apertures are designed to allow the brace to fit for around 95% of malleoli found generally in the population.

The shape of the malleoli together with the particular materials used are selected to provide the necessary fixation or grip force about the ankle so that the instrument can be push-fit attached to a patient. The instrument is at least partially self-locating as the spring force exerted by the resilient material of the brace causes the brace to lock onto the ankle in a generally unique position.

It will be appreciated that in other applications of the invention, the members will have different shapes and dimensions in order to capture other bony parts of features to which the brace is to be attached.

Also, the material of the brace is selected to provide sufficient flexibility and resilience of the brace to allow it to fit around 95% of ankle sizes present in the population.

The brace is asymmetric as the first and second members have different shapes and sizes to take into account the slightly differing anatomy of the malleoli on the left and right sides of the ankle. The instrument can be used on left hand and right hand ankles simply by removing the brace from the instrument, rotating the brace through 180 degrees and re-attaching the brace to the instrument. Therefore, a single instrument can be used on both the left hand side and right hand side ankles of a patient. Further, the brace is designed to automatically position the alignment guide with the tibia of a typical patient. Typically, the tibia is positioned approximately 60% from the lateral side and 40% from the medial side of the leg. Therefore, the brace is designed so that the alignment guide 50 is attached to the brace in a position approximately 60% from the lateral side and 40% from the medial side of the brace (wherein the medial and lateral sides of the brace are defined by the different shaped and sized members to accept the slightly different anatomy of the medial and lateral side malleolus). Hence, when the instrument is initially attached to a patient, the brace is automatically positioned at a 60/40 ratio in the medial-lateral direction of the patient so that the alignment guide is automatically approximately aligned with the tibia.

In other embodiments, the 60%-40% (or any other ratio) positioning of the brace can be also achieved by using two different materials for the same component. For example the brace can be made of two materials having different stiffness or mechanical properties, one for the medial and the other for the lateral portion. In this way, the brace can be self centering for any given ankle size.

The remainder of the parts of the instrument can be made of various plastics materials, such as ABS, polypropylene, polyurethane, polyethylene, polycarbonate and nylon, except for various spring and pin parts of the clamps and clips which are made of suitable bio-compatible metals. Further, the cutting guide 40 is typically made of a suitable bio-compatible metal, such as stainless steel or similar.

Use of the instrument will now be described. As explained above the invention is not limited to the particular external tibial alignment guide described, but can be used in other types of surgical instruments and similarly the method of use of the invention is not limited to specific instrument described.

Initially, the surgeon brings the instrument generally into alignment with the patient's lower leg, by generally aligning the longitudinal axis of the instrument with the longitudinal axis, i.e., in the inferior-superior direction, of the patient's lower leg. The brace is positioned anterior to and over the ankle, near to the malleoli. The surgeon can check whether the brace is in the correct orientation for the patient's ankle, and if not, then the brace can be removed, rotated by 180° and then re-attached to the instrument. The brace is pushed over the patient's ankle and the brace deforms to allow the ankle to enter into the mouth of the generally re-entrant or C-shaped cross sectional space defined by the members. The leading curved edges of the members rides over the malleoli until the brace is pushed sufficiently onto the ankle for the members to pass over to the posterior side of the malleoli and encircle the malleoli. Curved edge 84 of member 82 will be brought into abutment with a part of the front of the shin of the patient, so as to hold the alignment guide at a preferred position away from the tibia.

As the brace is made of a resilient material, the brace will automatically clamp about and securely grip the ankle. Also, as the holes in the members are shaped to accept the bony parts of the malleoli the brace will automatically settled about the malleoli and hence self-locate itself in a particular position. The grip exerted by the resilient material of the brace will also prevent the brace from moving significantly, unless sufficient force is applied to remove the brace by pulling it away from the ankle in a generally anterior direction. Further, as the alignment guide is located 60:40 along the width of the brace, the alignment guide is likely to be largely aligned with the middle of the tibia, absent any abnormal anatomy.

The surgeon, can then operate the base clamp 60 and slide the alignment guide in the medial-lateral direction, if required, in order to fine tune the positioning of the guide 50. The surgeon can also operate clip 79 in order to extend or reduce the length of the guide, if required, so as to position the cutting block at the correct height relative to the distal part of the tibia for making the tibial cut. The surgeon can also tilt the upper part of the alignment guide to change the cutting angle of the cutting block by operating pivot mechanism clamp 98, and pushing the upper part of the guide and cutting block toward the tibia. The surgeon can view the current degree of tilt displayed through aperture 96 to determine when the desired degree of tilt has been achieved. As the curved member has a radius of curvature which terminates generally in the upper plate of cutting block, the overall length of the guide, that is the separation between the cutting guide slot of the cutting block and the brace does not substantially change, when the upper part is tilted and so the height of the cutting block relative to the tibia does not need changing.

The cutting block can then be pinned in place. The spring clip 120 can then be operated to release the cutting block and the surgeon can pull on the instrument to release the brace from around the malleoli. Hence, the surgeon can more easily attach and release the instrument using the brace. The instrument also provides greater adjustability and ease of use.

The invention claimed is:

1. A surgical instrument for aligning a component relative to a bone, the bone contained within a limb, the instrument comprising:
    a brace for releasable attachment to the limb;
    a lower part attached to the brace and extending from the brace along a longitudinal axis;
    a housing slidably attached to the lower part along the longitudinal axis, the housing comprising a curved member that extends away from the longitudinal axis; and
    a second part that is slidable relative to the lower part along the longitudinal axis and is slidably attached to the curved member, the second part comprising a cylindrical portion disposed at least partially about the lower part and a sleeve disposed at least partially about the curved member, the sleeve being pivotable from a first position, whereat the cylindrical portion is aligned with the longitudinal axis and a second position, whereat the cylindrical portion is not aligned with the longitudinal axis.

2. The instrument of claim 1, further comprising a component attached to the second part, wherein the curved member has a radius of curvature and movement of the second part relative to the curved member does not substantially change a distance measured from the radius of curvature of the curved member to a defined point on the component.

3. The instrument of claim 2, wherein the component is a cutting block having a cutting slot.

4. The instrument of claim 1, wherein the sleeve is slidably mounted on the curved member.

5. The instrument of claim 1, wherein a portion of the housing is hollow and slidable along the longitudinal axis of the lower part.

6. The instrument of claim 1, further comprising a clamp for maintaining the position of the second part relative to the housing.

7. The instrument of claim 1, wherein the housing includes a scale for displaying the relative degree of tilt between the second part and the housing.

8. The instrument of claim 1, wherein the brace projects away from the longitudinal axis in a first direction and the curved member of the housing projects outwardly away from the longitudinal axis in a second direction generally opposite the first direction.

9. The instrument of claim 1, further comprising a base slidably mounted to the lower part at a first location and attached to the brace at a second location.

10. The instrument of claim 1, wherein, when the second part is in the first position, at least a portion of one of the second part and the housing is disposed within the other of one of the second part and the housing.

11. The instrument of claim 1, wherein, the second part comprises an elongate portion, and the elongate portion is aligned with the longitudinal axis when the second part is in the first position.

12. The instrument of claim 1, further comprising a component attached to the second part, wherein the second part is pivotably attached to the housing.

13. The instrument of claim 12, wherein the second part is pivotably attached to the housing at a location between the component and the brace along the longitudinal axis.

* * * * *